United States Patent [19]

Peterson et al.

[11] Patent Number: 5,427,907
[45] Date of Patent: Jun. 27, 1995

[54] ASSAY FOR EQUINE INFECTIOUS ANEMIA VIRUS

[75] Inventors: Darrell Peterson, Chesterfield; Peisheng Hu, Richmond, both of Va.

[73] Assignee: Virginia Commonwealth University, Richmond, Va.

[21] Appl. No.: 485,338

[22] Filed: Feb. 23, 1990

[51] Int. Cl.6 .................. G01N 33/543; G01N 33/569
[52] U.S. Cl. ........................................ 435/5; 435/7.9; 435/7.93; 435/7.95; 436/518
[58] Field of Search ................ 435/7.1, 7.93, 7.2, 435/5, 7.9, 7.95; 436/811, 518

[56] References Cited

U.S. PATENT DOCUMENTS 4,806,467 2/1989 Porter et al. ................... 435/793

OTHER PUBLICATIONS

Romerser (1983) Equus 116:18–20.
O'Rourke et al (1988) Antuiral Antiglycoproten and Neutralization . . . J Gen Viral 69:667–674.
Ball et al (1988) Lentivirus Antigen purification and characterization . . . J V. rol Meth. 19:265–277.
Rushlow et al (1986) Lentivirus Genomei Organization . . . Virol. 155:309–321.
Hussain et al (1987) Antigenic Analysis of EIAU . . . J Virol 61;2956–2961.
Shoemann et al (1987) Comparison of Recombmant . . . Anal. Biochem 161:370–379.
Clark (1980) The Experimental Foundation of Modern Immunology, J W & Sons P. 5–6.

*Primary Examiner*—David Saunders
*Attorney, Agent, or Firm*—Kirkpatrick & Lockhart

[57] ABSTRACT

The present invention is directed toward the use of a synthetic peptide as the antigen in an immunoassay for the detection of antibodies against the equine infectious anemia virus in the serum of horses. The synthetic peptide corresponds to the amino acid sequence of an antigenic portion of the GP-45 envelope protein of the equine infectious anemia virus. The immunoassay may be a direct second antibody immunoassay, a one or two step sandwich immunoassay, or a competitive immunoassay.

10 Claims, 3 Drawing Sheets (The First Bar In Each Is Peptide 1
The Second Bar In Each Is Peptide 2
The Third Bar In Each Is Peptide 3)

ASSAY FOR EQUINE INFECTIOUS ANEMIA VIRUS

BACKGROUND OF THE INVENTION

1. Field of the Invention

The present invention relates to a synthetic peptide and its use in an immunoassay for the detection of Equine Infectious Anemia (EIA) viral infection.

2. Description of the Prior Art

Equine Infectious Anemia is a viral disease, commonly known as swamp fever, which primarily affects horses and ponies. There is no known cure for the disease. Diagnosis and isolation is the only way to control the disease.

The accepted way to diagnose the presence of EIA has been to detect the presence of antibodies specific for the disease in the serum of affected animals using the Coggins or agar gel diffusion test described in U.S. Pat. No. 3,929,982 and U.S. Pat. No. 3,932,601. In the Coggins test, a prepared antigen is placed alongside the serum to be tested in an agar or gel medium. If EIA antibodies are present in the test serum, they will diffuse toward the antigen forming a precipitin line in the agar medium where they eventually meet.

This methodology is inherently insensitive in that the EIA antigen may be contaminated with non-EIA antigens during its preparation. Antibodies against non-EIA antigens may be present in the test serum and can react with the non-EIA antigens forming a variety of nonspecific precipitin lines. Even if the prepared EIA viral antigen can be purified, the Coggins test is labor intensive and demanding of considerable expertise in interpretation of results. The Coggins test procedure is also slow to yield results; it takes twenty-four to forty-eight hours for the formation of clearly visible precipitin lines.

Porter, U.S. Pat. No. 4,806,467, discloses a method for detecting the EIA virus using a competitive enzyme-linked immunoabsorbent assay incorporating a purified viral antigen and a monoclonal antibody. To obtain antigen, the EIA virus must first be cultured. The antigen is the p26 core protein of the EIA virus and is obtained through (purification of the cultured virus by a variety of means well known in the art. Immunizing mice with the antigen will produce hybridomas which will produce the monoclonal antibody specific to the p26 core antigen. The technique of culturing a virus increases the likelihood that the assay will yield false positive results since the virus may be contaminated with other forms of protein. Additionally, the EIA virus is hard to culture, making the Porter approach difficult for large scale production.

The use of a synthetic peptide in an enzyme linked (immunosorbent assay for the detection of human immunodeficiency virus (HIV) is disclosed in Shoeman, R. L. et al., *Analytical Biochemistry* 161:370-379 (1987). HIV and the EIA virus are members of the retrovirus family but have dissimilar structures and distinct amino acid sequences.

It is an object of the present invention to provide an assay for the detection of the equine infectious anemia virus which may be easily and quickly performed utilizing stable reagents which may be produced in sufficient amounts at a low cost. It is a further object of this invention to provide a pure source of antigen for use in such an assay to ensure accurate results.

SUMMARY OF THE INVENTION

The present invention provides a synthetic peptide which has an amino acid sequence at least a portion of which corresponds to that of an antigenic site of an equine infectious anemia virus. The antigenic site is preferably located in the envelope protein portion of the equine infectious anemia virus. The present invention also provides a method of detecting the presence of antibodies to the equine infectious anemia virus using as antigen the synthetic peptide of the present invention.

The method of the present invention includes the steps of synthesizing a peptide having an amino acid sequence at least a portion of which corresponds to an antigenic site on an equine infectious anemia virus, and exposing a selected amount of the peptide to a selected amount of equine test serum for a first period of time sufficient to allow any equine infectious anemia viral antibodies present in the test serum to bind with the peptide, forming a peptide-antibody complex. The method further includes the steps of exposing the peptide-antibody complex to a selected amount of a labeled conjugate for a second period of time sufficient to allow the conjugate to bind with the peptide-antibody complex and detecting the presence of the labeled conjugate which bound with the peptide-antibody complex.

The conjugate may be labeled with a radioactive element, such as Iodine, or may be magnetically labeled. The conjugate may also be an anti-horse antibody such as sheep anti-horse immunoglobulin which will recognize and bind to an equine infectious anemia viral antibody, a purified equine infections anemia viral antigen or a synthetic peptide, such as the synthetic peptide of the present invention, having an amino acid sequence corresponding to an antigenic site on an equine infectious anemia virus. The conjugate is preferably labeled with an enzyme selected from the group consisting of horseradish peroxidase and alkaline phosphatase. The step of detecting an enzyme labeled conjugate includes the additional step of adding a substrate, such as an orthophenylenediamine/hydrogen peroxide solution, in an amount sufficient to react with the enzyme label to convert the substrate to a sufficient amount of a product to produce a color change that is visible to the naked eye. The method may further include the step of quantifying the amount of the enzyme-labeled conjugate bound to the peptide-antibody complex by measuring the absorbance of the product of the enzymatic reaction using a spectrophotometer.

An alternate method of the present invention includes the steps of exposing the peptide of the present invention to a solid phase support, such as a multi-well polyvinyl microtitre plate, for a first period of time sufficient to permit the peptide to bind to the support and subsequently removing unbound peptide. The alternate method further comprises the steps of mixing a selected amount of labeled anti-EIA antibody with a selected amount of equine test serum, adding the mixture to the solid phase support containing the peptide to expose the peptide to the mixture for a second period of time sufficient to permit the peptide to bind to the antibodies in the mixture, removing any unbound antibodies from the support, and detecting the amount of labeled anti-EIA antibody bound to the peptide. In this method, the amount of labeled anti-EIA antibody is less than the amount of antibody in the selected amount of test serum.

BRIEF DESCRIPTION OF THE FIGURES

The present invention will be understood better by reference to the Figures in which.

Figure 1:
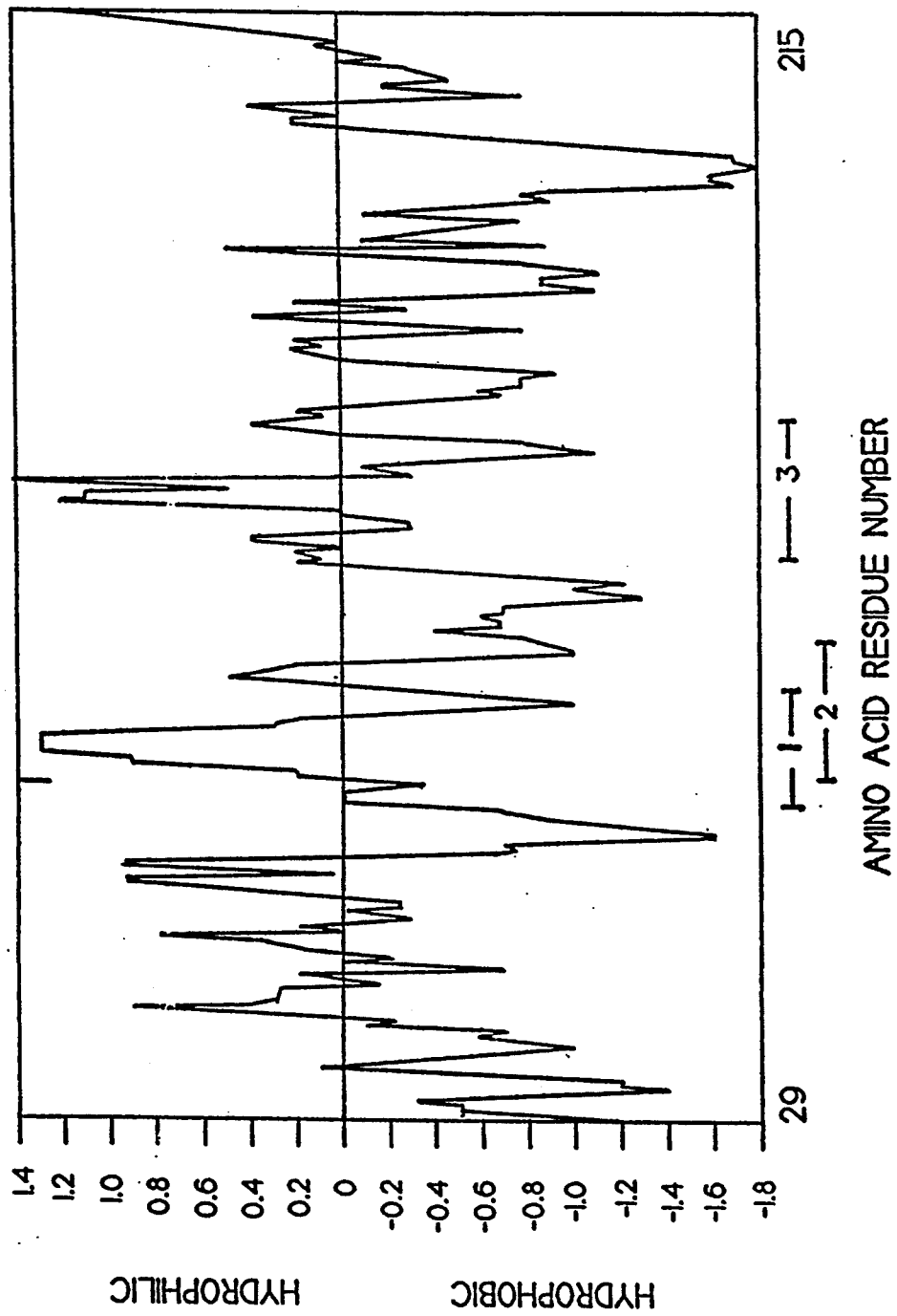
FIG. 1 is a hydropathy profile of the GP-45 protein portion of the envelope protein of an equine infectious anemia virus.
Figure 2:
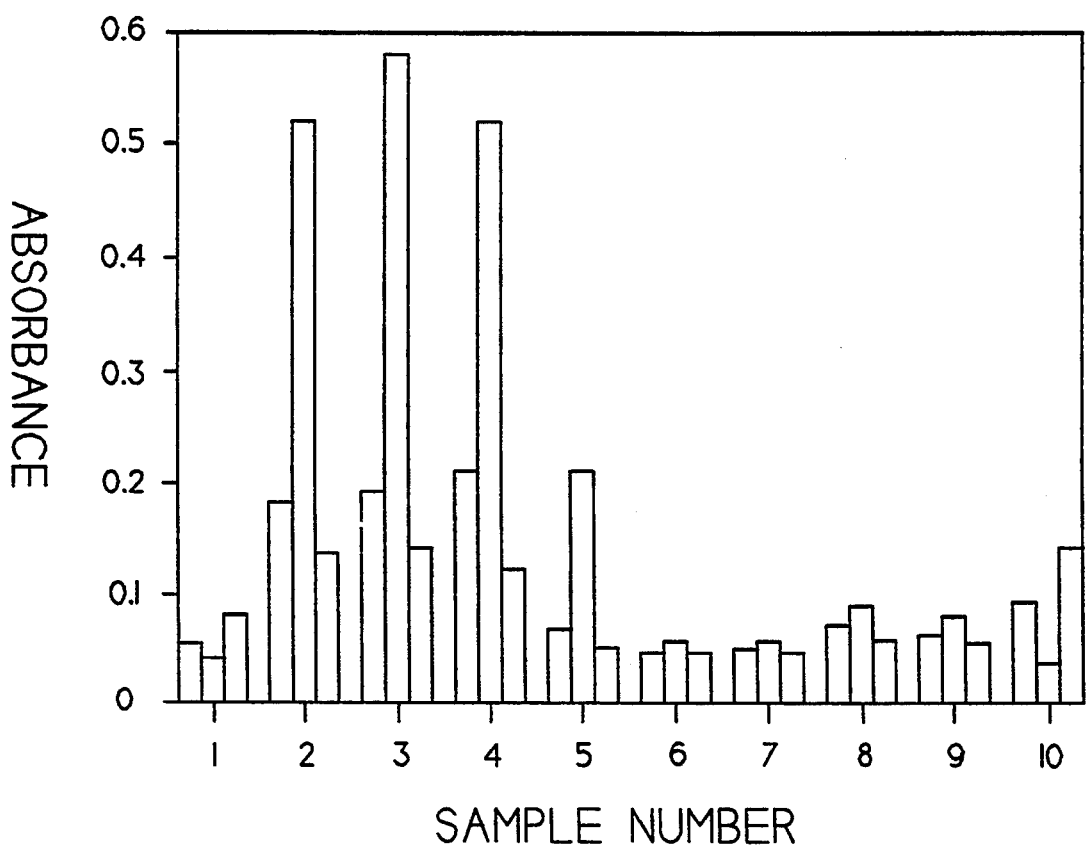
FIG. 2 shows the results of the use of each of three synthetic peptides in a solid phase enzyme linked immunosorbant assay against ten test samples of equine serum.
Figure 3:
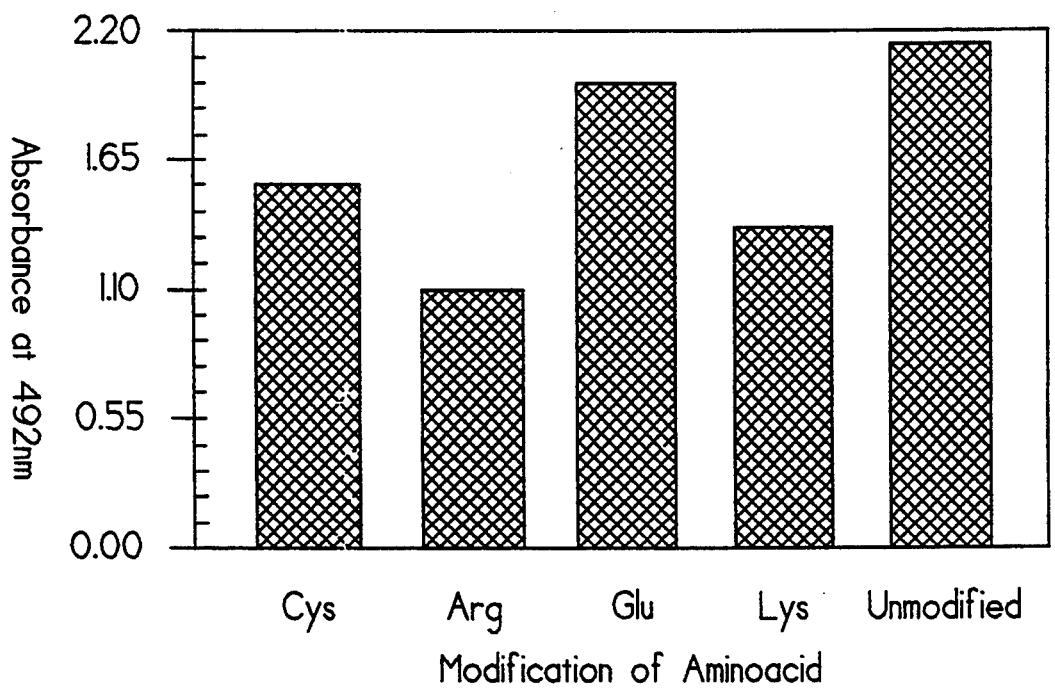
FIG. 3 shows the effects of chemical modification of four amino acids in the synthetic peptides upon the peptides' function as antigen.

DETAILED DESCRIPTION OF THE PREFERRED EMBODIMENTS

The present invention provides a synthetic peptide for use as the antigen in an immunoassay for the detection of antibodies in the sera of affected animals indicative of Equine Infectious Anemia (EIA) viral infection. The amino acid sequence of the peptide of the present invention comprises any sequence which corresponds to that of an antigenic site on the virus, and preferably those sequences which correspond to antigenic sites located in the envelope protein portion of the equine infectious anemia virus. Two particular amino acid sequences have been found to provide very good results. One, which consists of the amino acids comprising residues 68–91 of the GP-45 protein, follows:

glutamine-threonine-histidine-alanine-aspartic acid-valine-glutamine-leucine-leucine-lysine-glutamic acid-arginine-glutamine-glutamine valine-glutamic acid-glutamic acid-threonine-phenylalanine-asparagine-leucine-isoleucine-glycine-cysteine. (Referred to hereinafter as peptide 1).

The other, which consists of the amino acids comprising residues 76–99 of the GP-45 protein, follows:

leucine-leucine-lysine-glutamic acid-arginine-glutamine-glutamine-valine-glutamic acid-glutamic acid-threonine-phenylalanine-asparagine-leucine-isoleucine-glycine-cysteine-isoleucine-glutamic acid-arginine-threonine-histidine-valine-phenylalanine-cysteine. (Referred to hereinafter as peptide 2).

The methodology used-to discover peptides 1 and 2 will be discussed in further detail hereinbelow.

In one embodiment of the method of the present invention, the synthetic peptide, preferably peptide 2, is used as the antigen in an indirect double antibody immunoassay. The peptide is added to a solid phase support and incubated for a sufficient time to ensure that the peptide is bound to the support. Any peptide which does not bind is removed. A substance, known as a blocker, which will not react with EIA viral antibodies is added to the support. The equine test serum is added to the support and allowed to incubate for a period of time sufficient to permit any EIA antibodies present in the test serum to bind to the peptide. After incubation, unbound test serum antibodies are removed. Labeled conjugate is added which binds to the peptide-antibody complex. Following a time sufficient to allow such binding, any unbound labeled conjugate is removed. The amount of bound labeled conjugate is detected by means appropriate for the type of labeling employed. A high level of bound conjugate indicates a positive result, i.e., the presence of EIA viral antibodies. A low level of bound conjugate indicates a negative result.

A variety of commercially available solid phase supports may be used to bind the peptide. For purposes of this invention, any multi-well microtitre plate, such as a Costar® 96 well polyvinyl microtitre plate, will work well. The direct binding of equine antibodies present in the test serum to the solid phase support is likely to result in a false positive reading. To prevent such binding, the blocker is used to fill any empty sites on the support which did not bind synthetic peptide. Any substance which will not react with EIA viral antibodies will function as a blocker.

A conjugate is some species which will recognize and bind with the test serum EIA viral antibodies. The conjugate may be a second antibody, referred to as an anti-horse antibody for its ability to recognize and bind with any other horse antibody, including an EIA viral antibody. Alternatively, the conjugate may be purified equine infectious anemia viral antigen, or the synthetic peptide of the present invention which has an amino acid sequence corresponding to an antigenic site of an equine infectious anemia virus. The conjugate may be labeled using a variety of labeling means, including but not limited to: radiolabeling, enzyme labeling, fluorescent labeling, and magnetic labeling. Radioactive Iodine is a well known radiolabeling agent. If enzyme labeling is the labeling means chosen, the conjugate is labeled with an enzyme preferably selected from the group consisting of horseradish peroxidase and alkaline phosphatase. Other enzymes may be employed.

When an enzyme label is used, the labeled conjugate is detected by adding an amount of a substrate which will recognize and react with the enzyme label to form a product that will produce a color change visible to the naked eye. The presence of color indicates a sufficient level of test serum antibodies to indicate infection. An absence of color is an indicator of a lack of infection, as the animal did not produce a significant number of antibodies to the virus. Hence, the labeled conjugate had few antibodies, if any, to bind with and was subsequently removed from the support. There are a variety of both peroxidase substrates and phosphatase substrates which will react with horseradish peroxidase and alkaline phosphatase enzymes, respectively, to form a colored product. A preferred peroxidase substrate is an ortho-phenylenediamine/hydrogen peroxide solution.

The intensity of the color of the product may be quantified using a spectrophotometer to read absorbance. However, measuring the absorbance is not necessary to obtain an accurate reading of the results of the assay.

EXAMPLE 1

The assay was performed using only peptide 2 to test blind 131 samples in a series of four test runs.

Step 1: Preparation of the solid phase support

In order to prepare a peptide coated plate, the peptide was dissolved in a 0.1M solution of sodium bicarbonate/sodium carbonate buffer, having a pH of 9, at a concentration of 5 μg/ml. This buffer, known as the coating buffer, was prepared by dissolving 1.59 g of sodium carbonate, 2.93 g of sodium bicarbonate and 0.2 g of sodium azide in distilled water to make up a total volume of 1.0 liter. This buffer may be stored at room temperature for not more than two weeks. One hundred microliters of the peptide in buffer solution was added to each well of a 96 well polyvinyl microtitre plate. The plate was incubated in a humid chamber overnight, or approximately 18 hours. The peptide solution was removed by washing the plate with phosphate buffered saline (PBS). A solution of equine albumin (100 mg/ml) in PBS was added to the plate and was allowed to incubate for one hour at room temperature. Following incubation, the plate was washed with PBS and allowed to air dry. The resulting plate was peptide coated and any sites not containing peptide were covered with equine albumin blocker. A plate prepared in this manner will remain stable for at least six months with no loss of sensitivity.

Step 2: Performance of the assay

Equine test serum in a 1:10 dilution in 10% equine albumin in PBS was added directly to one of the wells of the peptide coated plate to expose the peptide to the test serum and was allowed to incubate at room temperature for 60 minutes to allow antibodies present in the sera to bind with the peptide to form a peptide-antibody complex. After incubation, the serum was removed by washing the peptide coated plate five times with PBS. Fifty microliters of horseradish peroxidase labeled sheep-anti-horse immunoglobin diluted in 10% equine albumin in PBS was added to the peptide coated plate and allowed to incubate for 60 minutes to allow the conjugate to bind with the peptideantibody complex. The plate was washed five times with PBS to remove any unbound second antibody. A substrate solution was prepared by dissolving 40 mg of orthophenylenediamine in 100 ml of a phosphate-citrate buffer at pH 5.0 and adding 40 μl of 30% hydrogen peroxide. The substrate solution is light sensitive and must be made up freshly before use and must be used immediately. One hundred microliters of substrate solution was added to the plate and color development was allowed to proceed for 5–30 minutes. Fifty microliters of a solution of $H_2SO_4$ (2.5M) was added to stop the reaction between the enzyme and the substrate. The color of the solution was observed.

Two groups of samples were observed. Those giving high color were judged to be positive, and those with low color were judged to be negative. These results were found to be 100% correct when the key was provided by the supplier of the samples.

In all of the following examples, the results shown in parentheses are those indicated by the supplier of the samples which were tested. The results not in parentheses are laboratory results.

| | Test Run 1 | |
|---|---|---|
| No. | A492 nm | Result |
| 1 | 0.866 | + (+) |
| 2 | 0.104 | − (−) |
| 3 | 1.232 | + (+) |
| 4 | 0.201 | − (−) |
| 5 | 1.327 | + (+) |
| 6 | 0.143 | − (−) |
| 7 | 1.674 | + (+) |
| 8 | 1.562 | + (+) |
| 9 | 0.211 | − (−) |
| 10 | 1.982 | + (+) |
| 11 | 0.146 | − (−) |
| 12 | 1.892 | + (+) |
| 13 | >2.0 | + (+) |
| 14 | 0.210 | − (−) |
| 15 | 1.256 | + (+) |
| 16 | 0.168 | − (−) |
| 17 | >2.0 | + (+) |
| 18 | 1.765 | + (+) |
| 19 | 0.124 | − (−) |
| 20 | 0.176 | − (−) |

| | Test Run 2 | |
|---|---|---|
| No. | A492 nm | Result |
| 21 | 0.132 | − (−) |
| 22 | 1.567 | + (+) |
| 23 | 0.143 | − (−) |
| 24 | 1.863 | + (+) |
| 25 | 1.684 | + (+) |
| 26 | 0.107 | − (−) |
| 27 | 0.141 | − (−) |
| 28 | >2.0 | + (+) |
| 29 | 0.148 | − (−) |
| 30 | 1.798 | + (+) |
| 31 | 0.112 | − (−) |
| 32 | 0.131 | − (−) |
| 33 | 0.140 | − (−) |
| 34 | 1.962 | + (+) |
| 35 | 0.164 | + (+) |
| 36 | 0.119 | − (−) |
| 37 | 0.111 | − (−) |
| 38 | >2.0 | + (+) |
| 39 | 0.122 | − (−) |
| 40 | >2.0 | + (+) |
| 41 | 0.128 | − (−) |
| 42 | 0.164 | − (−) |
| 43 | 0.143 | − (−) |
| 44 | 1.863 | + (+) |
| 45 | 1.952 | + (+) |
| 46 | 0.125 | − (−) |
| 47 | 0.167 | − (−) |
| 48 | 1.786 | + (+) |
| 49 | 0.127 | − (−) |
| 50 | >2.0 | + (+) |
| 51 | 0.122 | − (−) |
| 52 | 0.118 | − (−) |
| 53 | 0.128 | − (−) |
| 54 | >2.0 | + (+) |
| 55 | 1.876 | + (+) |
| 56 | >2.0 | + (+) |
| 57 | 0.143 | − (−) |
| 58 | 1.654 | + (+) |
| 59 | 0.134 | − (−) |
| 60 | 0.130 | − (−) |
| 61 | 0.133 | − (−) |

| | Test Run 3 | |
|---|---|---|
| No. | A492 nm | Result |
| 62 | 0.145 | − (−) |
| 63 | >2.0 | + (+) |
| 64 | 0.118 | − (−) |
| 65 | 1.678 | + (+) |
| 66 | 1.987 | + (+) |
| 67 | 0.121 | − (−) |
| 68 | 0.133 | − (−) |
| 69 | >2.0 | + (+) |
| 70 | 0.117 | − (−) |
| 71 | 1.864 | + (+) |
| 72 | 0.128 | − (−) |
| 73 | 0.122 | − (−) |
| 74 | 0.118 | − (−) |
| 75 | 1.893 | + (+) |
| 76 | 0.125 | − (−) |
| 77 | 0.124 | − (−) |
| 78 | 0.140 | − (−) |
| 79 | >2.0 | + (+) |
| 80 | 0.129 | − (−) |
| 81 | >2.0 | + (+) |
| 82 | 0.122 | − (−) |
| 83 | 0.142 | − (−) |

-continued

Test Run 3

| No. | A492 nm | Result |
|---|---|---|
| 84 | 0.131 | − (−) |
| 85 | >2.0 | + (+) |
| 86 | >2.0 | + (+) |
| 87 | 0.135 | − (−) |
| 88 | 0.126 | − (−) |
| 89 | 1.769 | + (+) |
| 90 | 0.126 | − (−) |
| 91 | >2.0 | + (+) |
| 92 | 0.133 | − (−) |
| 93 | 0.121 | − (−) |
| 94 | 0.142 | − (−) |
| 95 | >2.0 | + (+) |
| 96 | >2.0 | + (+) |
| 97 | >2.0 | + (+) |
| 98 | 0.120 | − (−) |
| 99 | 1.794 | + (+) |
| 100 | 0.116 | − (−) |
| 101 | 0.120 | − (−) |

Test Run 4

| No. | A492 nm | Result |
|---|---|---|
| 102 | 0.088 | − (−) |
| 103 | 0.053 | − (−) |
| 104 | 0.041 | − (−) |
| 105 | >2.0 | + (+) |
| 106 | 0.020 | − (−) |
| 107 | >2.0 | + (+) |
| 108 | >2.0 | + (+) |
| 109 | *0.365 | + (+) |
| 110 | >2.0 | + (+) |
| 111 | >2.0 | + (+) |
| 112 | 0.039 | − (−) |
| 113 | *0.438 | + (+) |
| 114 | 0.033 | − (−) |
| 115 | >2.0 | + (+) |
| 116 | >2.0 | + (+) |
| 117 | >2.0 | + (+) |
| 118 | >2.0 | + (+) |
| 119 | >2.0 | + (+) |
| 120 | >2.0 | + (+) |
| 121 | >2.0 | + (+) |
| 122 | 0.063 | − (−) |
| 123 | >2.0 | + (+) |
| 124 | >2.0 | + (+) |
| 125 | >2.0 | + (+) |
| 126 | >2.0 | + (+) |
| 127 | 0.043 | − (−) |
| 128 | 0.039 | − (−) |
| 129 | 0.017 | − (−) |
| 130 | >2.0 | + (+) |
| 131 | 0.068 | − (−) |

131 samples    62 positive    69 negative    100% correct

The samples in Test Run 4 marked by asterisks gave low values of Absorbance at 492 nm, but were still well above the expected values of negative samples. These samples are designated as low positives. The supplier of the test samples, The National Veterinary Scienes Lab of Ames, Iowa, currently does not count these two samples in certifying accuracy of test results, as many test laboratories were unable to detect a positive result using the approved Coggins test method.

It is likely that some amino acids may not be as critical to the function of the peptide as others. In an effort to determine which amino acids of the EIA peptide may be modified without significantly affecting the peptide's ability to function as antigen in the assay, some chemical modifications to certain amino acids were carried out. Cysteines were modified by reduction for 4 hours with a 100 fold molar excess of 2-mercaptoethanol at pH 8 followed by aklylation with a 2 fold excess of iodoacetate over total thiol concentration. Arginines were modified by reaction with a 75 fold molar excess of 1,2 cyclohexanedione in 0.1M borate buffer, pH 9.0, for 3 hours. Lysines were modified by reaction with a solution containing 5M formaldehyde and 10 mM sodium cyanoborohydride, in 50mM sodium phosphate buffer, pH 7.0, for 2 hours. Glutamic Acids were modified by reaction with a 10 fold molar excess of glycine methyl ester and a 1 molar excess of carbodiimide.

FIG. 3 shows that the modification of the glutamic acid amino acid does not result in more than a minor loss of antigenic activity, as measured by comparison of the Absorbance values obtained in assays using the unmodified peptide to those using the modified glutamic acid. Thus, it would seem that glutamic acid does not play a critical role in the antigenic activity of the peptide. It may be modified or replaced during synthesis with no adverse effect upon the function of the peptide as antigen. As shown in FIG. 3, modification of cysteine, lysine, or arginine does not result in a total loss of antigenic activity.

It is believed at this time that not all of the amino acids of the peptide sequence are critical to its antigenic function. While their presence may provide optimum antigenic activity, it will be appreciated that selected amino acids in the peptide sequence may be modified or substituted for, while maintaining a peptide that still functions as claimed.

Further, since modification of these four amino acids does not result in a total loss of antigenic activity, the functional groups of these amino acids may be modified for use in coupling the peptide to an enzyme for labeling and to other solid phases. This-observation suggests that the synthetic peptide may be used in a second type of assay, known as a sandwich immunoassay.

The assay is carried out in the same manner as the indirect double antibody immunoassay. However, the labeled conjugate is a purified form of EIA viral antigen, rather than a second anti-horse antibody. The antigen will recognize and bind with any EIA antibodies present in the test serum. Labeled synthetic peptide may be used as the conjugate in this type of assay. A sandwich immunoassay may be performed in two steps: adding test serum and incubating and subsequently adding labeled conjugate and incubating. Alternatively, a sandwich immunoassay may be performed with one incubation wherein the test serum is mixed with labeled conjugate then added in one step to be exposed to the synthetic peptide.

EXAMPLE 2

This example describes the use of the synthetic peptide in a two-step sandwich immunoassay.

Step 1: Preparation of an enzyme labeled peptide solution.

Five mg of horseradish peroxidase was dissolved in 0.2 ml of 0.1M phosphate buffered saline at pH 6.8 containing 1.25% glutaraldeyde. The solution was allowed to incubate overnight and was dialyzed against normal saline solution. The peroxidase solution was adjusted to pH 9.6 by suitable known means and 1 mg of EIA synthetic peptide 2 was added. The solution was allowed to incubate for 8 hours at room temperature and then dialyzed against saline. This solution is then added to 1 ml of 10% equine albumin.

Step 2: Performance of the assay

The assay was performed in a two step procedure, that is, with two incubations.

A peptide 2-coated plate was prepared as in Example 1. Fifty microliters of equine test serum was added to one well of the peptide coated plate and allowed to incubate for 5 minutes. The plate was then washed 5 times with PBS solution. Fifty microliters of an appropriate dilution, empirically determined to be approximately 10 μg/ml, of the enzyme labeled peptide solution was added and allowed to incubate for 5 minutes. The plate was then washed 5 times with PBS solution. A peroxidase substrate was added and color was allowed to develop. Fifty microliters of a solution of $H_2SO_4$ (2.5M) was added to stop the reaction between the enzyme and the substrate.

As in the indirect second antibody immunoassay, the presence of color indicates the presence of antibodies directed against the EIA virus. Negative samples give little, if any, color. Color intensity may be quantified by using a spectrophotometer and reading Absorbance at 492 nm.

EXAMPLE 3

This example describes the use of the synthetic peptide in a one-step sandwich immunoassay. A peptide 2-coated plate was prepared as in Example 1. An enzyme labeled peptide solution was prepared as in Example 2. Fifty microliters of equine test serum was added to 50 μl of the enzyme labeled peptide solution. This mixture was added to one well of the plate. The plate was allowed to incubate at room temperature for 5 minutes. The plate was then washed 5 times with PBS solution. A peroxidase substrate was added. The color was allowed to develop and 2.5M $H_2SO_4$ was added in a quantity sufficient to stop the reaction between the enzyme and the substrate.

The presence of color indicates the presence of antibodies directed against the EIA virus. Negative samples give little, if any, color. Color intensity may be quantified by using a spectrophotometer and reading Absorbance at 492 nm.

Figure 4:
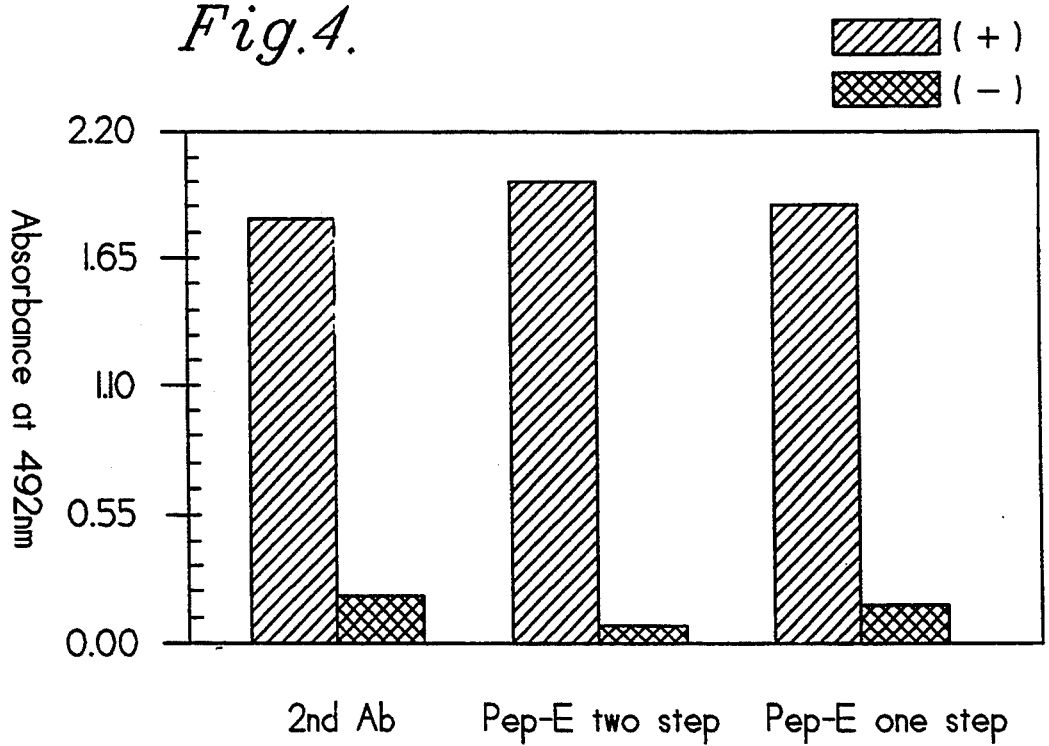
FIG. 4 is a comparison of the effectiveness of three immunoassay formats utilizing a synthetic peptide of the present invention.

FIG. 4 shows a comparison of the three assay formats shown previously by Examples 1, 2, and 3. The indirect second antibody method is designated 2nd Ab; Pep-E two step and Pep-E one step refer to the enzyme labeled peptide in a sandwich assay utilizing either a single or double incubation. As seen in FIG. 4, it is clear that all three types of assays work well providing a clear distinction in absorbance between positive and negative samples and the corresponding color change which is visible to the naked eye.

In an additional embodiment of this invention, an indirect double antibody immunoassay or a sandwich immunoassay may be performed wherein a synthetic peptide is bound to a solid phase filter material. Any unbound test serum antibodies or unbound labeled conjugate will automatically pass through the filter material. It will be appreciated that use of a filter material as the solid phase support eliminates the need for incorporating the specific steps of removal of unbound materials from the assay.

In a further embodiment of the present invention, a competition immunoassay is contemplated. A synthetic peptide is bound to a solid phase support with unbound peptide subsequently being removed. A known amount of labeled conjugate in the form of second anti-EIA antibody in relatively small concentration is added to the test serum. This mixture is added to the solid phase support containing bound peptide. Both the labeled second antibodies and the EIA viral antibodies present in the test serum compete for the binding sites available on the synthetic peptide. All antibodies which do not bind to the peptide are removed and any labeled second antibody which does bind is determined by means appropriate for the type of label which is employed.

If a high level of labeled conjugate is detected, the test serum does not contain EIA viral antibodies. Conversely, when low levels of labeled conjugate are detected, the test serum contains EIA viral antibodies which take up the binding sites on the peptide so that labeled conjugate cannot bind in an appreciable amount. Therefore, the interpretation given the results of a competition immunoassay is the opposite of that given the results of an indirect or sandwich immunoassay. A high level of bound labeled conjugate is a negative result and a low level is a positive result.

Immunoassays utilizing a synthetic peptide from this invention may be performed satisfactorily at any temperature within the range of about 4° C. to about 45° C. It is anticipated that this wide range of temperatures will facilitate field-use of the assay. Either undiluted equine test sera or a dilution of this serum made in 10% equine albumin in phosphate buffered saline may be used in the assay. Incubation times for exposing the peptide to the equine test sera and for exposing the peptide antibody complex to the conjugate may range from about 5 minutes to about 60 minutes. A five minute assay is performed on undiluted test serum. Longer assay times of up to about 60 minutes are used for sera which has been diluted 1:10 or greater. Concentrations of peptide in the range of about 0.1 μg/ml to 200 μg/ml will work in coating the solid phase support; however, optimal results are obtained with about 5 μg/ml concentrations or greater. It will be appreciated by those skilled in the art that enzyme labeling is an efficient and safe means of labeling antibody or antigen. Nonetheless, it is anticipated that a variety of labeling techniques, including but not limited to radiolabeling, fluorescent labeling and magnetic labeling, may be employed in the assay without changing the effectiveness and accuracy of the results.

The methodology used to discover peptides 1 and 2 will now be described. The choice of peptides 1 and 2 as the preferred synthetic peptides of the present invention for use in the assays described above involved analysis and experimentation to determine which amino acid sequences would provide the desired results.

It is known that a virus has both antigenic and non-antigenic regions. One may make a reasonable guess regarding the location of possible antigenic sites based upon certain known viral behaviors in conjunction with published information regarding the EIA virus. These target locations were chosen for peptide synthesis with the peptide then being tested for antigenic activity in an immunoassay to detect EIA viral antibodies.

The envelope protein portion of the EIA virus was chosen for investigation because it is known that the envelope proteins of other viruses contain many regions which exhibit antigenic activity. The complete genome of the envelope protein portion of the EIA virus has been sequenced. See Rushlow, K. et al., *Virology* 155:309–321 (1986). The amino acid sequence of the envelope protein can be predicted from this published gene sequence. The published amino acid sequence served as the starting point for experiments to determine the amino acid sequence of the synthetic peptide of the present invention.

The envelope protein is cleaved by the virus into two protein portions, known as GP-45 and GP-90. GP-90 is the larger of the two proteins and is known to exhibit antigenic variation, (See Rushlow, et al.), making peptides within this protein unsuitable for use in an immunoassay. The GP-45 protein was investigated to determine its most likely antigenic sites.

It is known that the first amino acid residue of the GP-45 protein begins a lipid spanning region which ends approximately at residue 29. The lipid spanning region is known to be hydrophobic and likely to be along the internal domain of the virus. Based on experience with other viruses, it has been found that hydrophilic regions are typically positioned adjacent to hydrophobic regions. Hydrophilic regions are likely to be external and thus potential antigenic sites.

FIG. 1 shows a computer generated hydropathy profile plotting the relative hydrophilicity and hydrophobicity of each amino acid of the protein which was used to determine the most likely location of the hydrophilic regions along the GP-45 protein. Several well defined peaks are observed in the hydrophilic region. The amino acid sequence corresponding to each peak is hydrophilic and, therefore, likely to be antigenic. Three of these amino acid sequences were chosen for peptide synthesis. It is anticipated that additional peptides corresponding to various other hydrophilic regions of the protein may also be synthesized. From laboratory experience, it is known that peptides from 20–30 amino acids in length provide favorable immunogens and often work as antigens.

The amino acid sequences chosen for synthesis and analysis were those of peptides 1 and 2, described above, and a third peptide, consisting of the amino acids comprising residues 111–133 of the GP-45 protein. The sequence of peptide 3 follows:

histidine-leucine-asparagine-glutamic acid-serine-threonine-glutamine-tryptophan-aspartic acid-aspartic acid-tryptophan-valine-serine-lysine-methionine-glutamic acid-aspartic acid-leucine-asparagine-glutamine-glutamic acid-isoleucine-leucine. (Referred to hereinafter as peptide 3).

Each of the three synthetic peptides was tested for antigenic activity by using each as the antigen in the following immunoassay to detect the presence of the EIA virus.

EXAMPLE 5

Ten samples of equine test sera were obtained for a blind study to test each of the three synthetic peptides, 1, 2, and 3, previously described to determine if the peptide would adequately function as an antigen for the detection of EIA viral antibodies. Ten samples were tested against each peptide using the procedure set forth in Example 1.

The results for each peptide in the ten sample test procedure are shown in FIG. 2. The first bar in each sample number is peptide 1, the second is peptide 2, and the third is peptide 3. The absorbance for the enzyme-substrate product of each sample is read at 492 nm.

Based upon the results shown in FIG. 2, it is clear that the use of peptide 2 coated plates in the immunoassay allows the test samples to be distinctly divided into two groups: group 1, consisting of samples 2,3,4, and 5 and group 2, consisting of samples 1, 6, 7, 8, 9, and 10. The group 1 samples show high levels of color and absorbance and indicate a positive test result.

The group 2 samples show little color development and low level absorbance and indicate a negative result. Based upon use of peptide 2 as antigen, it was predicted that samples 2, 3, 4, and 5 tested positive for EIA infection and samples 1, 6, 7, 8, 9 and 10 tested negative. These predictions were verified to be 100% correct upon confirmation by the supplier of the test samples. It is clear that peptide 2 allows for accurate and ready discrimination between positive and negative test samples.

The following table shows the accuracy of the test procedure and the spectrophotometer reading of absorbance of the test samples of the immunoassay of Example 5 when peptide 2-coated plates were used.

| | Test 1 | |
|---|---|---|
| No. | A492 nm | Result |
| 1 | 0.043 | − (−) |
| 2 | 0.516 | + (+) |
| 3 | 0.576 | + (+) |
| 4 | 0.518 | + (+) |
| 5 | 0.309 | + (+) |
| 6 | 0.033 | − (−) |
| 7 | 0.041 | − (−) |
| 8 | 0.048 | − (−) |
| 9 | 0.033 | − (−) |
| 10 | 0.037 | − (−) |

10 samples 4 positive 6 negative 100% correct

The results shown in parentheses are those indicated by the supplier of the samples which were tested. The results not in parenthesis are laboratory results.

Peptide 2 is preferred because it provides a clear distinction in color, visible to the naked eye, between positive and negative samples. This color distinction is not as striking when peptide 1 is used. However, it will be appreciated that the use of peptide 1 as antigen will give accurate results. A means for reading results more sophisticated than mere visual inspection, such as a reflective meter, must be employed.

The use of peptide 3 as antigen in the immunoassay does not appear to give accurate results. For example, it is known from the key provided by the supplier of the samples that sample 10 is negative and sample 5 is positive. Yet as shown in FIG. 2, with peptide 3 as antigen, sample 10 shows a substantially higher absorbance than does sample 5. Therefore, it is concluded that peptide 3 will not adequately function as antigen in an immunoassay for the detection of the EIA virus.

While the present invention has been described in connection with several examples, it will be understood that modifications and variations apparent to those of ordinary skill in the art are within the scope of the present invention.

What is claimed is:

1. A method of detecting the presence of antibodies to the equine infectious anemia virus in equine test samples which comprises the steps of:

(a) synthesizing a peptide having an amino acid sequence comprising:

leucine-leucine-lysine-glutamic acid-arginine-glutamine-glutamine-valine-glutamic acid-glutamic acid-threonine-phenylalanine-asparagine-leucine-isoleucine-glycine-cysteine-isoleucine-glutamic acid-arginine-threonine-histidine-valine-phenylalanine-cysteine;

(b) exposing said peptide to equine test samples in amounts and for a first period of time sufficient to allow any equine infectious anemia viral antibodies present in the test samples having the capacity to bind with an antigenic determinant on an equine infectious anemia virus, to bind with said peptide forming a peptide-antibody complex;

(c) exposing said peptide-antibody complex to a labeled conjugate selected from the group consisting of a purified equine infectious anemia viral antigen having the capacity to bind to said peptide-antibody complex, a second synthetic peptide having an amino acid sequence at least a portion of which corresponds to an antigenic determinant on an equine infectious anemia virus and having the capacity to bind to said peptide-antibody complex, and an anti-horse antibody which will recognize and bind to an equine infectious anemia viral antibody in amounts and for a second period of time sufficient to allow said conjugate to bind with any peptide-antibody complex formed to form labeled peptide-antibody complexes;

(d) detecting the presence of said labeled peptide-antibody complexes.

2. The method of claim 1 wherein said conjugate is labeled with an enzyme selected from the group consisting of horseradish peroxidase and alkaline phosphatase.

3. The method of claim 2 wherein the step of detecting said enzyme labeled conjugate comprises the additional step of: adding a substrate in an amount sufficient to react with said enzyme label to convert said substrate to a sufficient amount of a product to produce a color change that is visible to the naked eye.

4. The method of claim 3 wherein the substrate is an orthophenylenediamine/hydrogen peroxide solution.

5. The method recited in claim 3 further comprising the step of quantifying the amount of enzyme-labeled conjugate bound to said peptide-antibody complex by measuring the absorbance of said product using a spectrophotometer.

6. The method of claim 1 wherein said conjugate is labeled with a radioactive element.

7. The method of claim 6 wherein said radioactive element is Iodine.

8. The method of claim 1 wherein said conjugate is magnetically labeled.

9. A method of detecting the presence of antibodies to the equine infectious anemia virus in equine test samples which comprises the steps of:

(a) exposing a synthetic peptide having an amino acid sequence comprising:
leucine-leucine-lysine-glutamic acid-arginine-glutamine-glutamine-valine-glutamic acid-glutamic acid-threonine-phenylalanine-asparagine-leucine-isoleucine-glycine-cysteine-isoleucine-glutamic acid-arginine-threonine-histidine-valine-phenylalanine-cysteine to equine test samples in amounts and for a first period of time sufficient to allow any equine infectious anemia viral antibodies present in the test samples having the capacity to bind with an antigenic determinant on an equine infectious anemia virus, to bind with said peptide, thereby forming a peptide-antibody complex;

(b) adding a labeled conjugate selected from the group consisting of a purified equine infectious anemia viral antigen having the capacity to bind to said peptide-antibody complex, a second synthetic peptide having an amino acid sequence at least a portion of which corresponds to an antigenic determinant on an equine infectious anemia virus and having the capacity to bind to said peptide-antibody complex, and an anti-horse antibody which will recognize and bind to an equine infectious anemia viral antibody in amounts and for a second period of time sufficient to allow said conjugate to bind with any said peptide-antibody complex formed, thereby forming labeled peptide-antibody complexes;

(c) detecting the presence of said labeled peptide-antibody complexes.

10. A method of detecting the presence of antibodies to equine infectious anemia virus in equine test samples which comprises the steps of:

(a) exposing a synthetic peptide having an amino acid sequence comprising:
leucine-leucine-lysine-glutamic acid-arginine-glutamine-glutamine-valine-glutamic acid-glutamic acid-threonine-phenylalanine-asparagine-leucine-isoleucine-glycine-cysteine-isoleucine-glutamic acid-arginine-threonine-histidine-valine-phenylalanine-cysteine to a solid phase support for a first period of time sufficient to permit said peptide to bind to the support;

(b) removing unbound peptide;

(c) forming a mixture of a selected amount of labeled anti-EIA antibody with equine test sample in relative amounts sufficient to allow said labeled anti-EIA antibody and any equine infectious anemia viral antibody present in said test sample to compete for binding sites on said peptide;

(d) adding said mixture to the solid phase support containing said peptide to expose said peptide to said mixture for a second period of time sufficient to permit said peptide to bind to the antibodies present in said mixture;

(e) removing from said support any unbound antibodies from said mixture;

(f) detecting the amount of labeled anti-EIA antibody bound to said peptide.

* * * * *